(12) United States Patent
Kallok et al.

(10) Patent No.: US 8,177,801 B2
(45) Date of Patent: May 15, 2012

(54) METHOD AND APPARATUS FOR INCREASING ROTATIONAL AMPLITUDE OF ABRASIVE ELEMENT ON HIGH-SPEED ROTATIONAL ATHERECTOMY DEVICE

(75) Inventors: Michael J. Kallok, New Brighton, MN (US); Gary M. Petrucci, Long Lake, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 322 days.

(21) Appl. No.: 12/405,765

(22) Filed: Mar. 17, 2009

(65) Prior Publication Data
US 2009/0264908 A1 Oct. 22, 2009

Related U.S. Application Data

(60) Provisional application No. 61/046,145, filed on Apr. 18, 2008.

(51) Int. Cl.
*A61B 17/22* (2006.01)
(52) U.S. Cl. ...................................................... 606/159
(58) Field of Classification Search .................. 606/108, 606/114, 127, 128, 159, 170, 180, 191; 604/22
See application file for complete search history.

(56) References Cited

U.S. PATENT DOCUMENTS

| | | | |
|---|---|---|---|
| 5,312,427 A | | 5/1994 | Shturman |
| 5,554,163 A | | 9/1996 | Shturman |
| 5,584,843 A | * | 12/1996 | Wulfman et al. ............. 606/159 |
| 5,976,165 A | * | 11/1999 | Ball et al. ..................... 606/180 |
| 6,022,363 A | | 2/2000 | Walker et al. |
| 6,132,444 A | | 10/2000 | Shturman et al. |
| 6,217,595 B1 | | 4/2001 | Shturman et al. |

(Continued)

FOREIGN PATENT DOCUMENTS
WO WO2006/126176 11/2006
(Continued)

OTHER PUBLICATIONS http://www.merriam-webster.com/dictionary/clamped (p. 1) retrieved Sep. 8, 2011.*

(Continued)

*Primary Examiner* — Ryan Severson
*Assistant Examiner* — David Eastwood
(74) *Attorney, Agent, or Firm* — Winthrop & Weinstine, P.A.

(57) ABSTRACT

A high-speed atherectomy device is disclosed, for abrading a blockage (stenosis) in the interior of a lumen (artery). The device uses a rapidly rotating drive shaft that includes an eccentric abrasive element that has its center of mass laterally offset from the rotational axis of the drive shaft. As the drive shaft rotates, centrifugal force drives the eccentric abrasive element outward, so that it traces an abrading diameter at high rotational speeds that is larger than its rest diameter. The drive shaft includes counterweights on both sides of the abrasive element, which may stabilize operation at high rotational speeds. In some cases, the counterweights are also eccentric, with their centers of mass laterally offset from the rotational axis in the opposite direction as that of the abrasive element. The counterweights are longitudinally separated from the abrasive element, and in some cases, the separations are adjustable and/or controllable. In some cases, the guide wire may be retracted prior to or during the high-speed rotation of the drive shaft, with the retraction being to the distal counterweight, the abrasive element, the proximal counterweight, or beyond the proximal counterweight.

7 Claims, 12 Drawing Sheets

U.S. PATENT DOCUMENTS

| | | | |
|---|---|---|---|
| 2003/0125756 A1* | 7/2003 | Shturman et al. | 606/159 |
| 2005/0149083 A1* | 7/2005 | Prudnikov et al. | 606/159 |
| 2005/0209615 A1* | 9/2005 | Prudnikov et al. | 606/159 |
| 2008/0306498 A1* | 12/2008 | Thatcher et al. | 606/159 |
| 2009/0018564 A1* | 1/2009 | Shturman | 606/159 |
| 2009/0069829 A1* | 3/2009 | Shturman | 606/159 |
| 2009/0105736 A1* | 4/2009 | Prudnikov et al. | 606/159 |
| 2009/0182359 A1* | 7/2009 | Shturman | 606/159 |

FOREIGN PATENT DOCUMENTS

WO    WO 2006126176 A1 * 11/2006

OTHER PUBLICATIONS http://www.merriam-webster.com/dictionary/press%20fit (p. 1 ) retrieved Sep. 8, 2011.*

* cited by examiner

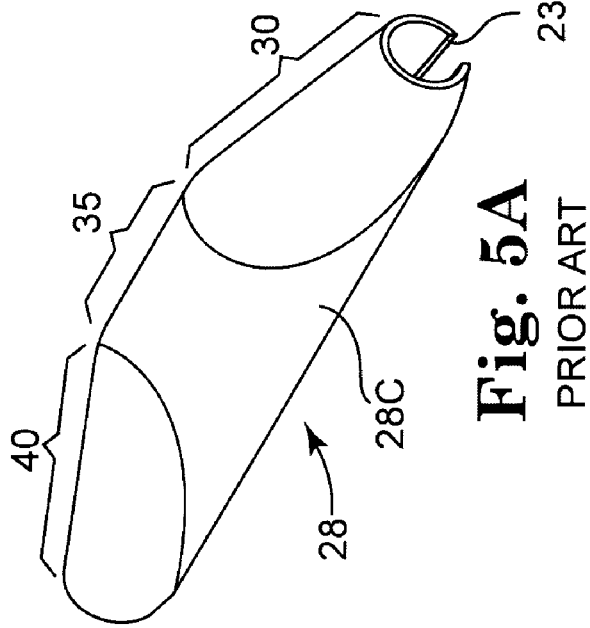
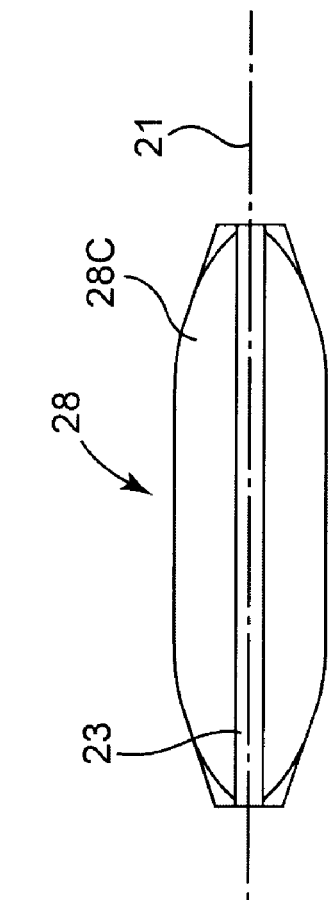
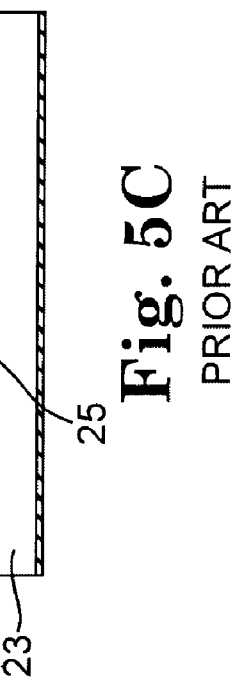
Fig. 5A PRIOR ART
Fig. 5B PRIOR ART
Fig. 5C PRIOR ART

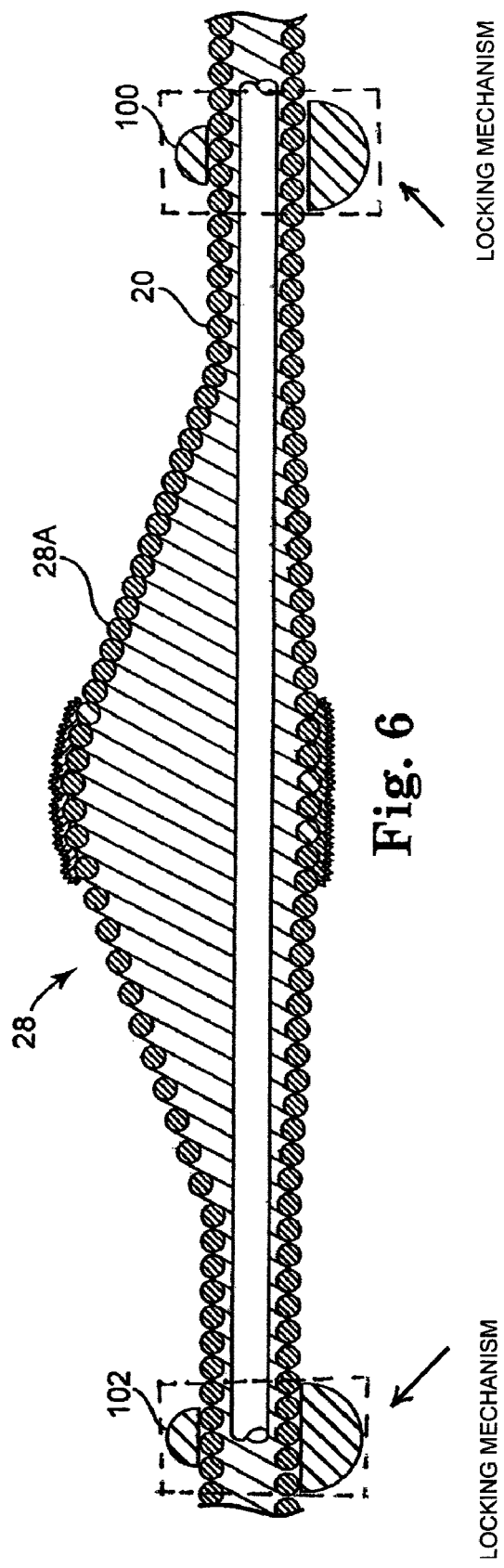

METHOD AND APPARATUS FOR INCREASING ROTATIONAL AMPLITUDE OF ABRASIVE ELEMENT ON HIGH-SPEED ROTATIONAL ATHERECTOMY DEVICE

CROSS-REFERENCE TO RELATED APPLICATIONS

The present application claims priority to provisional application No. 61/046,145, filed on Apr. 18, 2008 under the same title, the entire contents of which are incorporated herein by reference.

BACKGROUND OF THE INVENTION

1. Field of the Invention

The invention relates to devices and methods for removing tissue from body passageways, such as removal of atherosclerotic plaque from arteries, utilizing a high-speed rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis, which is a blockage of the stent that most frequently develops over a period of time as a result of excessive growth of scar tissue within the stent. In such situations, balloon angioplasty is not very effective within the stent, so an atherectomy procedure is the preferred procedure to remove the excessive scar tissue from the stent, thereby restoring the patentcy of the artery.

Several kinds of rotational atherectomy devices have been developed for attempting to remove stenotic material. In one type of device, such as that shown in U.S. Pat. No. 4,990,134 (Auth), a concentrically shaped ellipsoidal burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently, since the burr is of a fixed resting diameter, more than one size burr must be utilized to open an artery to the desired diameter. No other variables are disclosed by the Auth device that would allow sweeping a variable diameter, or a diameter larger than the burr's resting diameter, during high-speed rotation.

U.S. Pat. No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance". That is, given both the size and mass of the solid burr, it is infeasible to rotate the burr at the high speeds used during atherectomy procedures, i.e., rotational speeds within the range of about 20,000-200,000 rpm. Essentially, the center of mass offset from the rotational axis of the drive shaft would result in development of significant and undesirable centrifugal force, exerting too much pressure on the wall of the artery and creating too much heat and excessively large particles. As with Auth, the burr size is fixed and may require using more than one size burr to open the subject lumen to the desired diameter.

U.S. Pat. No. 6,132,444 (Shturman) and U.S. Pat. No. 6,494,890 (Shturman) disclose, inter alia, an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. The orbital rotational motion is primarily due to the offset of the center of mass of the enlarged eccentric section from the drive shaft's rotational axis. Since the enlarged eccentric section may comprise drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. The disclosures of U.S. Pat. Nos. 6,132,444 and 6,494,890 are each hereby incorporated by reference in their entirety.

BRIEF SUMMARY OF THE INVENTION

A first embodiment is a high-speed rotational atherectomy device for opening a stenosis in an artery having a given diameter, comprising: a guide wire having a maximum diameter less than the diameter of the artery; a flexible, elongated, rotatable drive shaft advanceable over the guide wire; an abrasive element disposed on the drive shaft; a proximal counterweight attached to the drive shaft and spaced apart proximally from the abrasive element by an adjustable proximal spacing; and a distal counterweight attached to the drive shaft and spaced apart distally from the abrasive element by an adjustable distal spacing.

A second embodiment is a method for generating a rotating diameter within a lumen with an abrasive section of a flexible drive shaft wherein the rotating diameter is larger than the resting diameter of the abrasive section, comprising: providing a guide wire with a diameter less than the diameter of the lumen; providing a flexible, elongated, rotatable drive shaft advanceable over the guide wire, the drive shaft having a rotational axis and an eccentric abrasive element; providing a proximal counterweight spaced a distance proximally from the eccentric abrasive element; providing a distal counterweight spaced a distance distally from the eccentric abrasive element; retracting the guide wire; and rotating the drive shaft at high speed.

A third embodiment is a method for generating a rotating diameter within a lumen with an abrasive section of a flexible drive shaft wherein the rotating diameter is larger than the resting diameter of the abrasive section, comprising: providing a guide wire with a diameter less than the diameter of the lumen; providing a flexible, elongated, rotatable drive shaft advanceable over the guide wire, the drive shaft having a rotational axis and an eccentric abrasive element, the abrasive element comprising an eccentric enlarged section of the drive shaft; providing a proximal counterweight spaced a distance proximally from the eccentric abrasive element, the proximal counterweight comprising an eccentric enlarged section of the drive shaft; providing a distal counterweight spaced a distance distally from the eccentric abrasive element, the distal counterweight comprising an eccentric enlarged section of the drive shaft; retracting the guide wire; and rotating the drive shaft at high speed.

BRIEF DESCRIPTION OF THE SEVERAL VIEWS OF THE DRAWINGS

FIG. 5A is a perspective view of a known eccentric abrading head, or crown, that attaches to the drive shaft.

FIG. 5B is a bottom view of a known eccentric abrading head, or crown, that attaches to the drive shaft.

FIG. 5C is a longitudinal cross-section view of a known eccentric abrading head, or crown, that attaches to the drive shaft.

FIG. 6 is a longitudinal cross-section view of an exemplary abrading head.

DETAILED DESCRIPTION OF THE INVENTION

Figure 1:
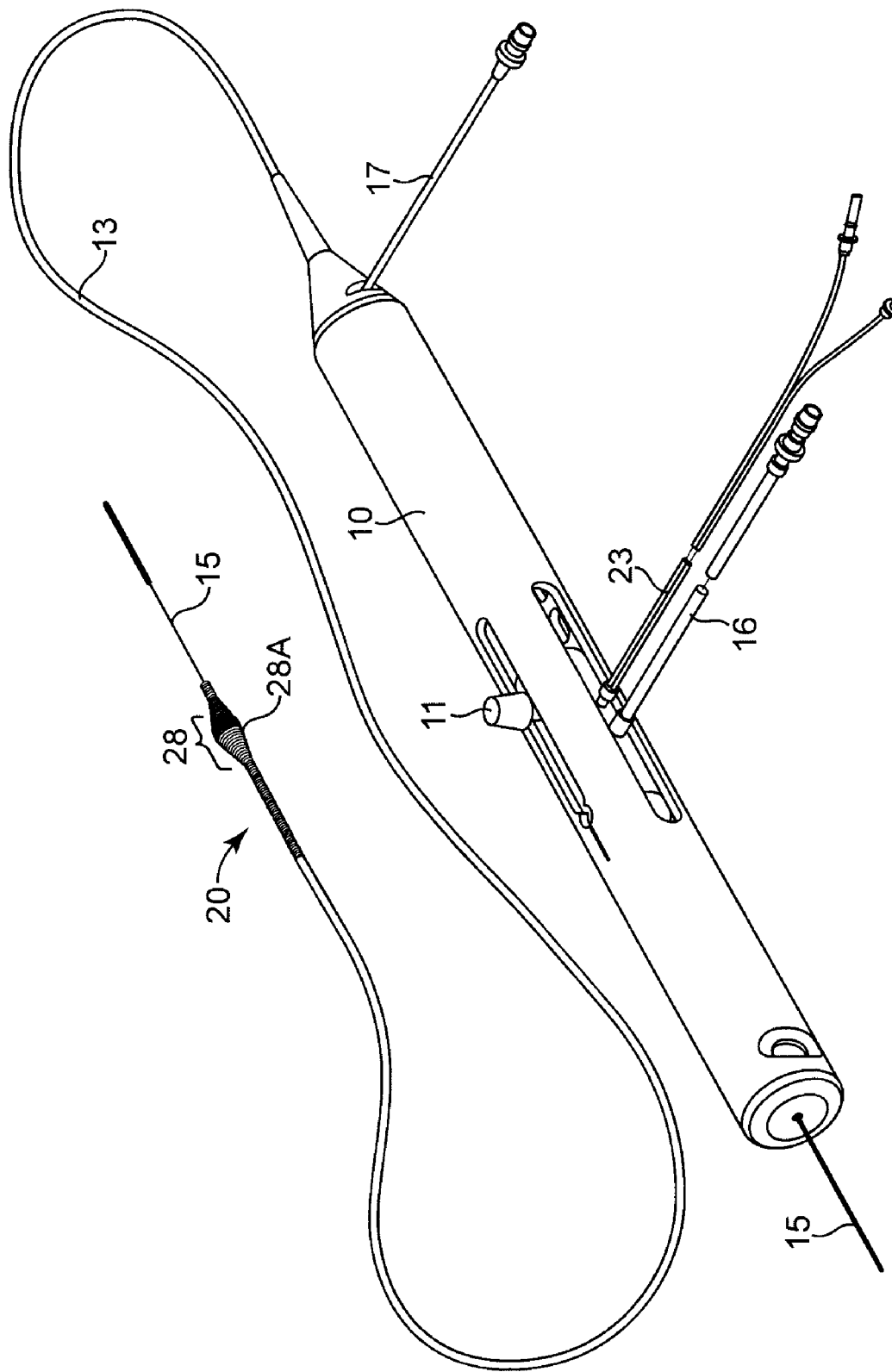
FIG. 1 is a perspective view of a non-flexible eccentric cutting head of a rotational atherectomy device.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

FIG. 1 illustrates a typical rotational atherectomy device. The device includes a handle portion 10, an elongated, flexible drive shaft 20 having an abrasive section 28 comprising an eccentric enlarged diameter section 28A, and an elongated catheter 13 extending distally from the handle portion 10. The drive shaft 20 and its eccentric enlarged diameter section 28 are constructed from helically coiled wire. The catheter 13 has a lumen in which most of the length of the drive shaft 20 is disposed, except for the enlarged diameter section 28A and a short section distal to the enlarged diameter section 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 23 may also be provided for monitoring the speed of rotation of the turbine and drive shaft 20. Details regarding such handles and associated instrumentation are well known in the industry, and are described, e.g., in U.S. Pat. No. 5,314,407, issued to Auth. The handle 10 also desirably includes a control knob 11 for advancing and retracting the turbine and drive shaft 20 with respect to the catheter 13 and the body of the handle.

Figure 2:
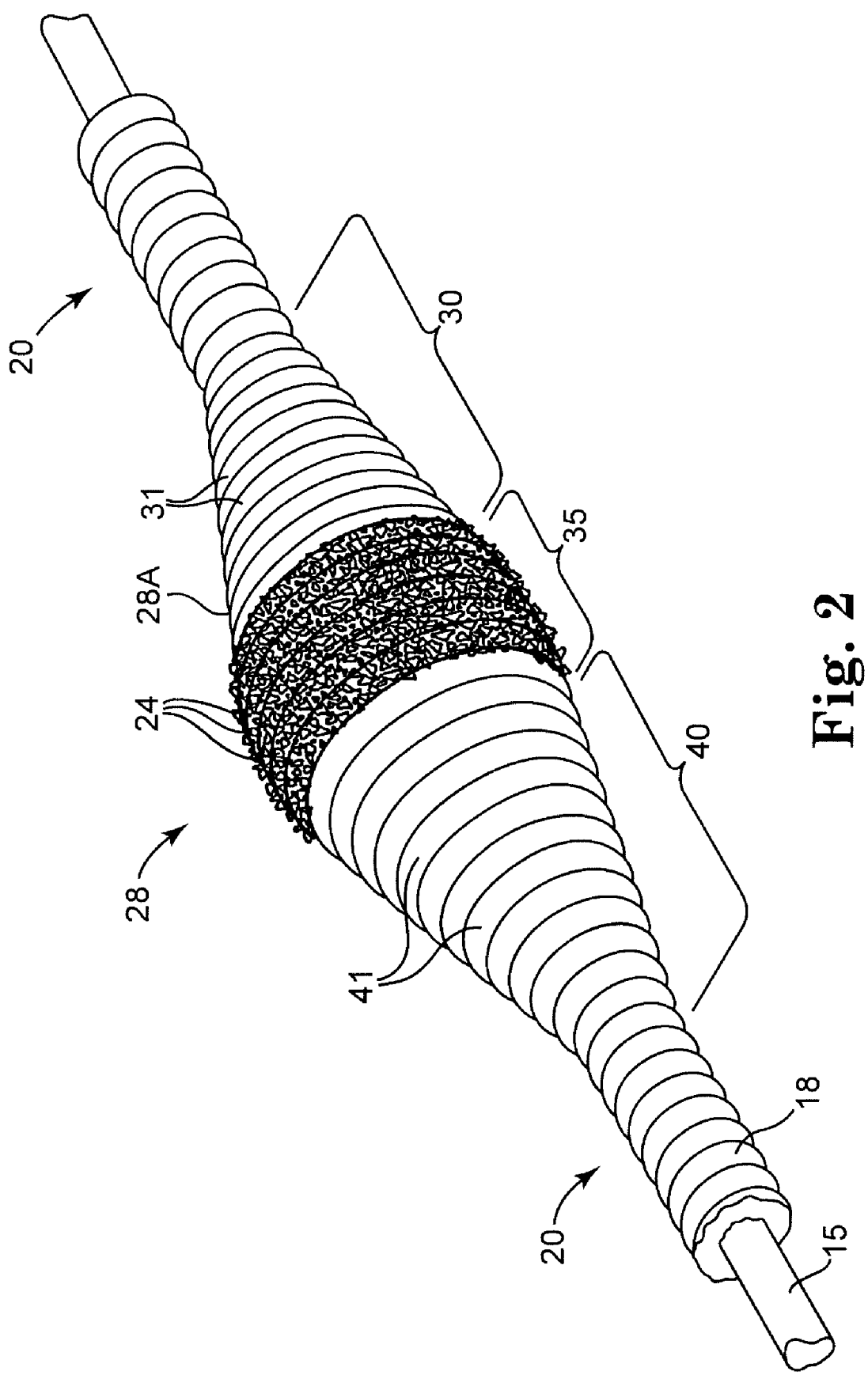
FIG. 2 is a perspective, broken-away view of a known, flexible, eccentric, enlarged section of the drive shaft.
Figure 3:
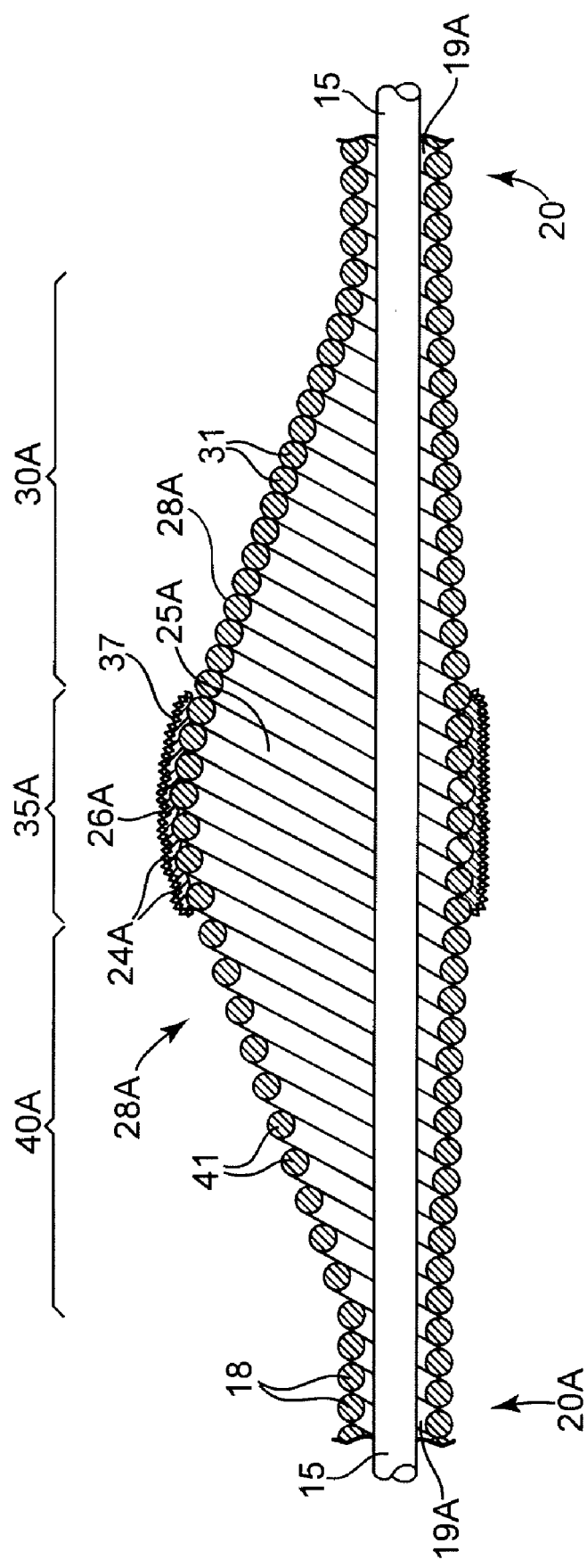
FIG. 3 is a broken-away, longitudinal cross-sectional view of a known, eccentric, enlarged section of the drive shaft.

FIGS. 2-3 illustrate details of abrasive section 28 comprising eccentric enlarged diameter section 28A. The drive shaft 20 is comprised of one or more helically wound wires 18 which define a guide wire lumen 19 and a hollow cavity 25 within the enlarged diameter section 28A. Except for the guide wire 15 traversing the hollow cavity 25, the hollow cavity 25 is substantially empty. Abrasive section 28 illustrated as eccentric enlarged diameter section 28A comprises proximal 30, intermediate 35 and distal 40 portions with a tissue removing surface 37 thereon. Wire turns 31 of the proximal portion 30 of the eccentric enlarged diameter section 28A preferably have diameters that progressively increase distally at a generally constant rate, thereby forming generally the shape of a cone. Wire turns 41 of the distal portion 40 preferably have diameters that progressively decrease distally at a generally constant rate, thereby forming generally the shape of a cone. Wire turns 36 of the intermediate portion 35 are provided with gradually changing diameters to provide a generally convex outer surface which is shaped to provide a smooth transition between the proximal and distal conical portions of the enlarged diameter section 28A of the drive shaft 20.

At least part of the abrasive section 28, illustrated as eccentric enlarged diameter section 28A (preferably the intermediate portion 35) comprises an external surface 37 capable of removing tissue. Preferably the tissue removing surface comprises a coating 37 of an abrasive material 24 to define a tissue removing segment of the drive shaft 20. The abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the wire turns of the drive shaft 20 by a suitable binder 26. Such attachment may be achieved using well known techniques, such as conventional electroplating or fusion technologies (see, e.g., U.S. Pat. No. 4,018,576). Alternately the external tissue removing surface may be simply a section of the wire turns which has been roughened to provide a suitable abrasive surface. In yet another variation, the external surface may be etched or cut (e.g., with a laser) to provide small but sharp cutting surfaces. Other similar techniques may also be utilized to provide a suitable tissue removing surface.

Figure 4:
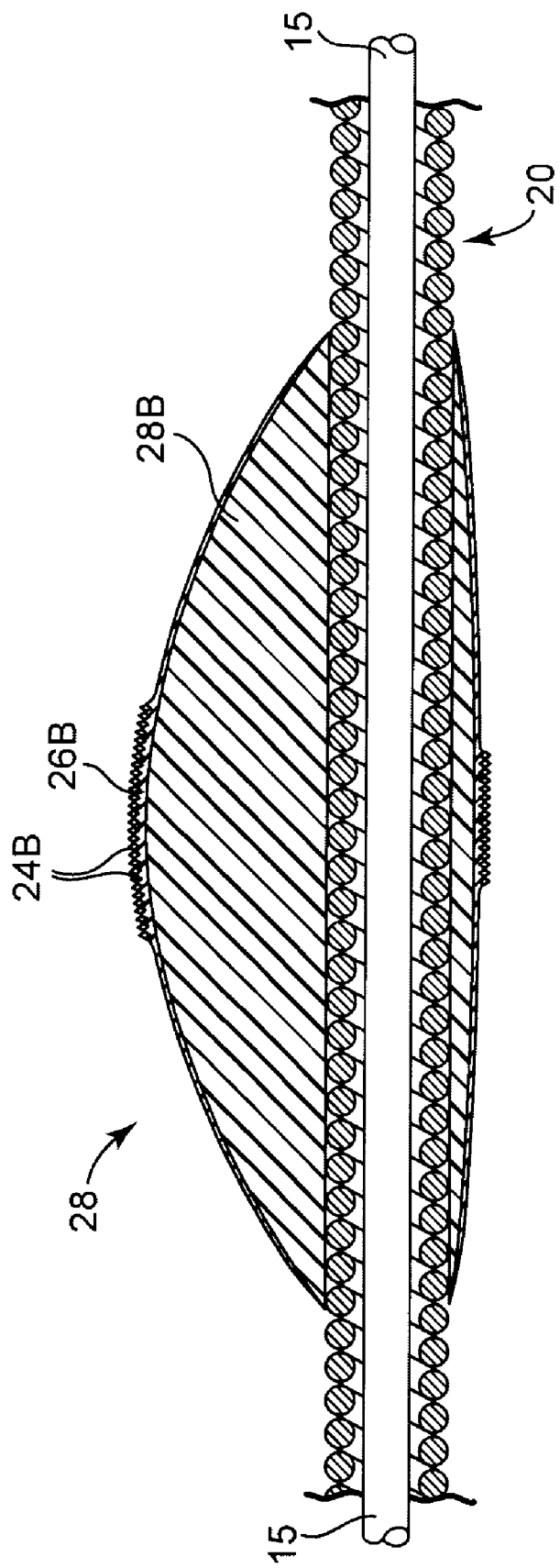
FIG. 4 is a broken-away, longitudinal cross-sectional view illustrating the flexibility of a known solid eccentric enlarged burr attached to the drive shaft.

FIG. 4 illustrates another type of known abrasive section 28, illustrated as an eccentric solid, or at least partially hollow, burr 28B. Solid, or at least partially hollow, abrasive burr 28B is attached to drive shaft 20 by means well known in the art and comprises a coating of an abrasive material 24 fixed to the surface by a suitable binder 26.

FIGS. 5A, 5B, and 5C illustrate another known abrasive surface 28, comprising an eccentric abrading head or crown 28C as described in U.S. application Ser. No. 11/761,128 to Thatcher et al., the disclosure of which is hereby incorporated by reference in its entirety. Lumen 23 is provided for crimping attachment to the drive shaft 20 and may comprise hollowed section 25 to assist in moving the center of mass either away from, or closer to, the drive shaft 20 axis of rotation. Abrasive section 28C comprises proximal 30, intermediate 35 and distal 40 portions, the proximal 30 and distal 40 portions sloping away from intermediate portion 35, represented as having a cylindrical shape.

Thus, one application comprises an abrasive section 28 that may, in turn, comprise an eccentric enlarged section 28A of the drive shaft, or an eccentric solid crown or abrading head 28C or eccentric burr 28B attached to the drive shaft, wherein the abrasive section 28 has a center of mass spaced radially from the rotational axis of the drive shaft 20, facilitating the ability of the device to open the stenotic lesion to a diameter substantially larger than the outer diameter of the abrasive section 28. This may be achieved by spacing the geometric center of the abrasive section 28, i.e., the eccentric enlarged diameter section of the drive shaft 20, or the eccentric solid abrading head or crown 28C, or burr 28B attached to the drive shaft 20, away from the rotational axis of the drive shaft 20. Alternatively, the center of mass of the abrasive section 28 may be radially spaced from the drive shaft's rotational axis by providing an abrasive section 28 that comprises a differential combination of materials, wherein one side of at least one of the abrasive section 28 comprises a more massive or denser material than the other side, which creates eccentricity as defined herein. As those skilled in the art will recognize, creation of eccentricity by differential use of materials within the structure of the abrasive section 28, e.g., a center of mass offset from the drive shaft's rotational axis, is applicable to any configuration of the abrasive section 28 discussed herein, whether concentric, eccentric, solid burr, partially hollow crown or abrading head or an enlarged section of the drive shaft, or the equivalent.

Further this application may comprise at least one counterweight located on, and fixedly attached to, the drive shaft to stimulate orbital motion of the eccentric abrasive section. One such at least one counterweight may be located proximal to the abrasive section, while another at least one counterweight may be located distal to the abrasive section.

In one application, as illustrated in FIG. 6, the abrasive section 28 is represented as eccentric enlarged diameter section 28A of the drive shaft 20. A distal counterweight 100 is located distally of the abrasive section 28 and a proximal counterweight 102 is located proximal to the abrasive section. Alternate applications may comprise only the distal counterweight 100 in operative combination with the abrasive section 28 or only the proximal counterweight 102 in operative combination with the abrasive section 28.

As illustrated in FIG. 6, the counterweights 100, 102 may be solid and eccentric burrs, though a number of alternatives are contemplated by the present application.

For example, one or both of the proximal and distal counterweights 100, 102 may comprise enlarged diameter sections of the drive shaft, formed in similar fashion as the enlarged eccentric diameter abrasive section 28A. In this application, the counterweights 100, 102 are essentially hollow, enlarged wire turns of the drive shaft 20, formed by use of a mandrel during the wire turn winding process. In the case where only one, either the proximal 102 or the distal 100, counterweight is an enlarged eccentric diameter abrasive section of the drive shaft 20, the remaining counterweight may be either concentric, i.e., center of mass collinear with the drive shaft's axis of rotation and comprising an enlarged diameter section of the drive shaft, a solid crown or at least partially hollow crown, or may be eccentric and comprising a solid burr or an at least partially hollow crown or abrading head.

Alternatively, one or both of the proximal and distal counterweights 100, 102 may be solid, as illustrated in FIG. 6 and attached to the wire turns of the drive shaft 20 by means well known to those skilled in the art. More alternatively, the proximal and distal counterweights 100, 102 may be at least partially hollow.

Still more alternatively, one or both of the counterweights 100, 102 may comprise differential combination of materials, wherein one side of at least one of the counterweights 100, 102 comprises a more massive or denser material than the other side, which creates eccentricity as defined herein. As those skilled in the art will recognize, creation of eccentricity by differential use of materials within the counterweights 100, 102, e.g., a center of mass offset from the drive shaft's rotational axis, is applicable to any configuration of the counterweights 100, 102 whether concentric, eccentric, solid burr, partially hollow crown or abrading head or an enlarged section of the drive shaft, or the equivalent.

In one application, the proximal and distal counterweights 100, 102 are substantially equivalent in overall mass as illustrated in FIG. 6, with each counterweight 100, 102 being roughly one half the overall mass of the abrasive section 28, wherein the proximal and distal counterweights 100, 102 are equidistant from the abrasive section 28, wherein the proximal and distal counterweights 100, 102 comprise centers of mass that are equidistant from the axis of rotation of the drive shaft 20 and wherein the proximal and distal counterweights 100, 102 comprise centers of mass are equidistant from the center of mass of the eccentric abrasive section 28. Alternative and equivalent mass distributions between the abrasive section 28 and the counterweight(s) for use in manipulating the orbital rotational diameter of the abrasive section 28 during high-speed rotation will present themselves readily to those skilled in the art.

Further, one or both of the counterweights (proximal and/or distal) 100, 102 may be concentric, i.e., spherical or ellipsoidal in profile or other concentric shape, with one or both of the counterweights (proximal and/or distal) 100, 102 having a center of mass that is substantially on, i.e., collinear with, the axis of rotation of the drive shaft 20.

Alternatively, one or both of the counterweights (proximal and/or distal) 100, 102 may be eccentric, i.e., one configuration may comprise the counterweights (proximal and/or distal) 100, 102 having a center of mass spaced radially from the rotational axis of the drive shaft 20 and aligned within the same longitudinal plane as the center of mass of the eccentric abrasive section 28 as shown in FIG. 6. The radial spacing of the centers of mass of the counterweights may be achieved by spacing the geometric center of each counterweight 100, 102 away from the rotational axis of the drive shaft 20, wherein the proximal counterweight 102 and the distal counterweight 100 each have a center of mass separated from the eccentric abrasive section's 28 center of mass by a rotational angle of 180 degrees as shown in FIG. 6. The centers of mass of the proximal 102 and distal 100 counterweights may be offset 180 degrees. This counterweighting arrangement stimulates orbital motion by the abrasive section 28 and facilitates the ability of the abrasive section 28 to sweep and open the stenotic lesion to a diameter substantially larger than the outer diameter of the resting eccentric enlarged diameter section 28.

An alternative application may comprise at least one of the counterweights 100, 102 having a center of mass that may, or may not be, separated from the abrasive section's 28 center of mass by a rotational angle of 180 degrees. One application may dampen the orbital rotational diameter of the abrasive section 28 during high-speed rotation by placing the center of mass of the at least one counterweight 100, 102 at a rotational angle of zero degrees from the center of mass of the abrasive section 28 center of mass. This may apply whether the abrasive section 28 is eccentric or concentric. For example, dampening may be achieved for an eccentric abrasive section 28 by attaching at least one eccentric counterweight 100, 102, wherein the centers of mass of the eccentric abrasive section 28 and the at least one eccentric counterweight 100, 102 are substantially collinear, i.e., with a rotational separation angle of substantially zero degrees.

Alternatively, if the abrasive section 28 is provided as concentric, with its center of mass on the rotational axis of the drive shaft 20, the at least one counterweight 100, 102 may be concentric, with center of mass also located on the rotational axis of the drive shaft 20. More alternatively, if the abrasive section 28 is provided as eccentric, with its center of mass located off the rotational axis of drive shaft 20, at least one counterweight may be provided having a center of mass located at a rotational angle of 180 degrees from the center of mass of the abrasive section 28. This application may be provided with the at least one counterweight being on the drive shaft 28 with, or without, a spaced distance between the at least one counterweight and the abrasive section 28.

Those skilled in the art will readily recognize that the respective arrangements of counterweight(s) and abrasive section 28, and centers of mass thereof disclosed herein both infra and supra, may apply to all forms, profiles and types of abrasive section 28 and counterweight(s) discussed herein to either stimulate, i.e., increase the rotational diameter, or dampen, i.e., decrease the rotational diameter, the orbital motion of the abrasive section 28.

Significantly, the present application may allow use of a smaller diameter abrasive section 28, in conjunction with proximal and distal counterweights 100, 102, while opening a lumen having a swept diameter equivalent to that of larger diameter abrasive sections 28 of the known references that do not comprise counterweights 100, 102 as described herein.

Those skilled in the art will recognize any number of combinations and permutations of these parameters for a given rotational speed of the drive shaft 20. The skilled artisan will recognize that modification of any of these parameters will either increase or decrease/dampen the diameter of the orbital path taken by the abrasive section. As such, the diameter of the orbital path may be customized for individual lumens.

Another application may comprise the abrasive section 28 comprising a concentric enlarged abrasive section of the drive shaft as described in U.S. Pat. No. 5,314,438 to Shturman, the disclosure of which is hereby incorporated by reference in its entirety. Alternatively, the abrasive section 28 of Shturman may comprise a concentric solid burr attached to the drive shaft as is well known in the art, see e.g., U.S. Pat. No. 4,990,134 to Auth. Concentric in this sense means that the abrasive section 28, either formed of the wire turns or by a solid or semi-solid, i.e., hollow burr comprises a profile that is spherical or ellipsoidal or other concentric shape, with the concentric abrasive section 28 having a center of mass that is substantially on, i.e., collinear with, the axis of rotation of the drive shaft 20.

Further this particular application comprises two counterweights 100, 102 attached to or mounted on the drive shaft 20 to stimulate orbital motion of the concentric abrasive section 28. Preferably, a distal counterweight 100 is located distally of the concentric abrasive section 28 and a proximal counterweight 102 is located proximal to the concentric abrasive section 28.

One or both of the proximal and/or distal counterweights 100, 102 may comprise enlarged diameter sections of the drive shaft, formed in similar fashion as the enlarged eccentric diameter abrasive section 28A illustrated in FIG. 6. In this application, the counterweights 100, 102 may be essentially hollow, enlarged wire turns of the drive shaft, formed by use of a mandrel during the wire turn winding process. In the case where only one, either the proximal 102 or the distal 102, counterweight is an enlarged eccentric diameter abrasive section of the drive shaft 20, the remaining counterweight may be either concentric, i.e., center of mass collinear with the drive shaft's axis of rotation and comprising an enlarged diameter section of the drive shaft 20, a solid burr or at least partially hollow abrading head, or may be eccentric and comprising a solid burr or at least partially hollow abrading head.

Alternatively, one or both of the proximal and distal counterweights 100, 102 may be solid and attached to the wire turns of the drive shaft 20 by means well known to those skilled in the art. More alternatively, the proximal and distal counterweights 100, 102 may be at least partially hollow.

In one application wherein the abrasive section 28 is concentric, the proximal and distal counterweights 100, 102 are substantially equivalent in overall mass, with each counterweight 100, 102 being roughly one half the overall mass of the concentric abrasive section 28, wherein the proximal 102 and distal 100 counterweights are equidistant from the concentric abrasive section 100, wherein the proximal and distal centers of mass are equidistant from the axis of rotation of the drive shaft 20 and wherein the proximal and distal centers of mass are equidistant from the center of mass of the concentric abrasive section 28.

The counterweights 100, 102 may be concentric, i.e., spherical or ellipsoidal in profile or other concentric shape, with the counterweights 100, 102 having a center of mass that is substantially on the axis of rotation of the drive shaft 20.

Preferably in this application comprising a concentric abrasive section 28, the counterweights 100, 102 are eccentric, i.e., the proximal 102 and distal 100 counterweights may have a center of mass spaced radially from the rotational axis of the drive shaft 20, each having the center of mass offset within the same longitudinal plane and within the same longitudinal plane as the center of mass of the concentric abrasive section 28 which is collinear with the axis of rotation. Moreover, the proximal 102 and distal 100 counterweight centers of mass may both be either above the axis of rotation or below the axis of rotation of the drive shaft 20 while both centers of mass are aligned within the same longitudinal plane, creating an "offset" between the center of mass of the abrasive section 28 and the centers of mass of the proximal 102 and distal 100 counterweights. The centers of mass of the proximal 102 and distal 100 counterweights may be offset 180 degrees, or other degree of offset as will be readily recognized by those skilled in the art, from each other around the axis of rotation of the drive shaft 20.

As with the eccentric abrasive section case, the concentric abrasive section case may achieve the radial spacing of the centers of mass of the eccentric case of the proximal 102 and distal 100 counterweights by spacing the geometric center of each counterweight 100, 102 away from the rotational axis of the drive shaft 20, wherein the proximal counterweight 102 and the distal counterweight 100 each have a center of mass separated from the concentric abrasive section's center of mass and within the same longitudinal plane. This counterweighting case stimulates orbital motion by the abrasive section 28 and facilitates the ability of the abrasive section 28 to sweep and open the stenotic lesion to a diameter substantially larger than the outer diameter of the resting concentric abrasive section 28. As above, the present application may allow use of a smaller diameter abrasive section 28, in conjunction with proximal 102 and distal 100 counterweights, while opening a lumen having a swept diameter equivalent to that of larger diameter concentric abrasive sections 28 of the known references.

Figure 7C:
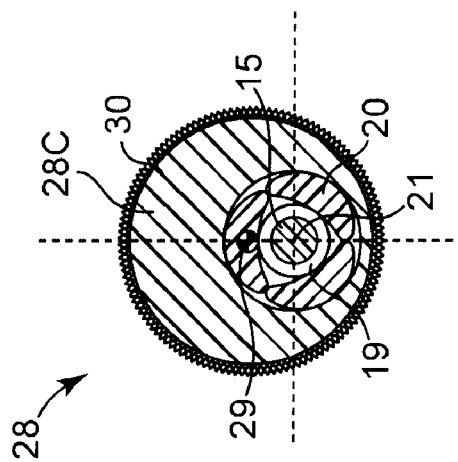
FIG. 7C is another cross-section view of an exemplary abrading head.
Figure 7B:
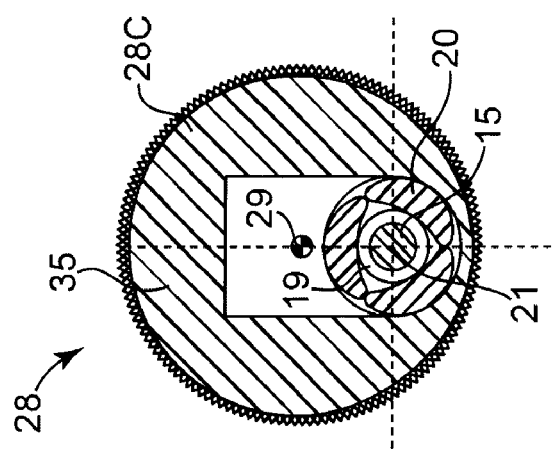
FIG. 7B is another cross-section view of an exemplary abrading head.
Figure 7A:
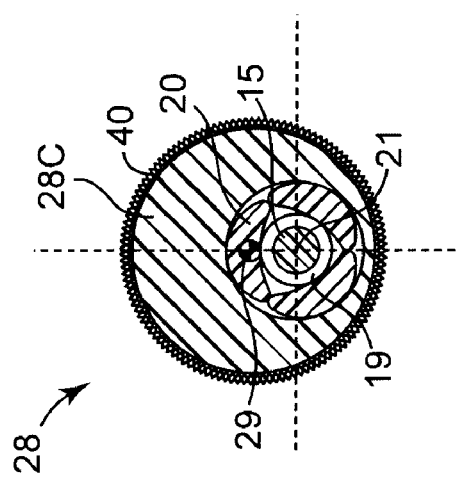
FIG. 7A is a cross-section view of an exemplary abrading head.

FIGS. 7A-7C depict the positions of the centers of mass 29 of three cross-sectional slices (shown as faces of transverse cross-sections) of the eccentric abrasive section 28, illustrated as an eccentric abrading head 28C as shown in FIGS. 5A, 5B and 5C during high-speed rotation with eccentric counterweights 100, 102 mounted on drive shaft 20 as described herein. The eccentric abrasive section 28 may be divided into many such thin slices, each slice having its own center of mass. FIG. 7B is taken at a position where the abrasive section 28 has its maximum cross-sectional diameter (which, in this case, is the maximum diameter of the intermediate portion 35 of the eccentric abrasive section 28), and FIGS. 7A and 7C are taken, respectively in the distal 40 and proximal 30 portions of the eccentric abrasive section 28. In each of these cross-sectional slices the center of mass 29 is spaced away from the rotational axis of the drive shaft, the rotational axis of the drive shaft 20 coinciding with the center of the guide wire 15. The center of mass 29 of each cross-sectional slice also generally coincides with the geometric center of such cross-sectional slice. FIG. 7B shows the slice having the greatest cross-sectional diameter. In this slice both the center of mass 29 and the geometric center are located the furthest (i.e., maximally spaced away) from the rotational axis of the drive shaft 20. Of course, the center of mass of the entire abrasive section 28 is a composite of the individual centers of mass of multiple slices of the enlarged diameter section, and the overall center of mass will, therefore, be closer to the axis of rotation of the drive shaft 20 than the center of mass of the slice depicted in FIG. 7B.

It should be understood that, as used herein, the word "eccentric" is defined herein to mean either a difference in location between the geometric center of the abrasive section 28 comprising eccentric enlarged diameter section 28A of the drive shaft 20, or an eccentric solid burr 28B, or an eccentric at least partially hollow crown or abrading head 28C, or the eccentric counterweight(s) and the rotational axis of the drive shaft, or to a difference in location between the center of mass of the eccentric abrasive section 28 comprising an eccentric enlarged diameter section 28A, an eccentric solid burr 28B and eccentric and at least partially hollow crown or abrading head 28C, or the eccentric counterweights 100, 102 and the rotational axis of the drive shaft 20. Either such difference, at the proper rotational speeds, will enable the abrasive section 28 to open a stenosis to a diameter substantially greater than the nominal diameter of the abrasive section 28. Moreover, for an eccentric abrasive section 28 having a shape that is not a regular geometric shape, the concept of "geometric center" can be approximated by locating the mid-point of the longest chord which is drawn through the rotational axis of the drive shaft and connects two points on a perimeter of a transverse cross-section taken at a position where the perimeter of the eccentric enlarged diameter section has its maximum length. Moreover, those skilled in the art will recognize that eccentricity as defined may be designed into an abrasive section 28 having a substantially concentric profile, but with one aspect of the profile being more massive than the rest by, e.g., hollowing out a portion of one side of the abrasive section 28.

Moreover, it should also be understood that concentric as used herein, is defined to mean an abrasive section 28 and/or counterweights 100, 102 that comprises a center of mass that is on, i.e., collinear with, the axis of rotation of the drive shaft 20 and a profile that is substantially symmetrical.

Figure 8:
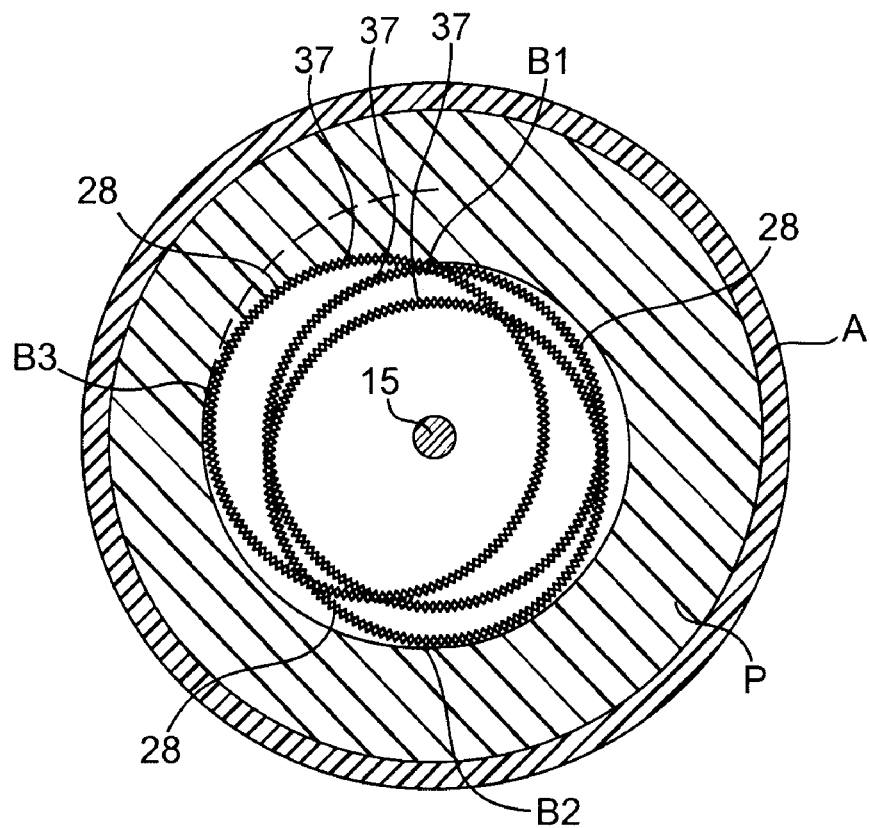
FIG. 8 is a transverse cross-sectional view illustrating three different positions of the rapidly rotating abrasive section of an eccentric rotational atherectomy device.
Figure 9:
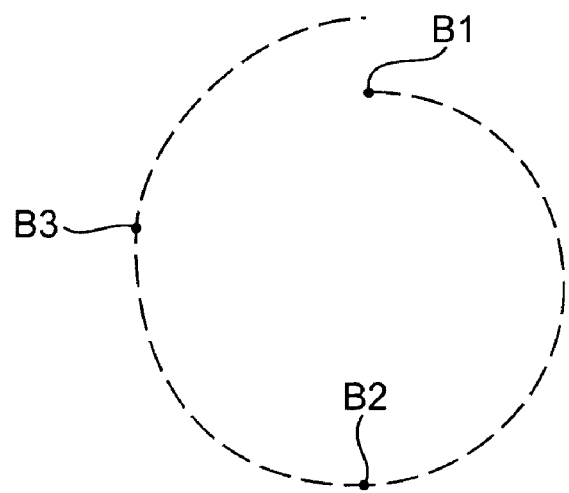
FIG. 9 is a schematic view corresponding to the three positions of the rapidly rotating abrasive section illustrated in FIG. 8.

FIGS. 8 and 9 illustrate the generally spiral orbital path taken by the eccentric abrading head 28, shown relative to the guide wire 15 over which the abrading head 28 has been advanced. The pitch of the spiral path in FIGS. 8 and 9 is exaggerated for illustrative purposes. In reality, each spiral path of the eccentric enlarged abrading head 28 removes only a very thin layer of tissue via the tissue removing surface 37, and many, many such spiral passes are made by the eccentric enlarged abrading head 28 as the device is repeatedly moved forward and backward across the stenosis to fully open the stenosis.

FIG. 9 shows schematically three different rotational positions of the eccentric enlarged abrading head 28 of a rotational atherectomy device. At each position the abrasive surface of the eccentric enlarged abrading head 28 contacts the plaque "P" to be removed. The three positions are identified by three different points of contact with the plaque "P", those points being designated in the drawing as points B1, B2, and B3. Notice that at each point it is generally the same portion of the abrasive surface of the eccentric enlarged abrading head 28 that contacts the portion of the tissue removing surface 37 that is radially most distant from the rotational axis of the drive shaft.

As mentioned above, the term "eccentric" is used to denote an element that has its center of mass laterally displaced from the rotational axis of the drive shaft, and the term "concentric" is used to denote an element that has its center of mass coincident with the rotational axis of the drive shaft. Likewise, an "abrasive section" may include any or all of an enlarged diameter section of the drive shaft (i.e., bigger coils in the "abrasive section"), a solid burr attached to or made integral with the drive shaft (and coils the same size throughout), an at least partially hollow crown attached to or made integral with the drive shaft (and coils the same size throughout), or coils that vary in size plus a burr or crown attached to or made integral with the drive shaft. In this manner, the terms "concentric"/"eccentric" and "abrasive section" may be used generally to describe various configurations of the atherectomy device.

As used herein, the term "element" may be used to denote any feature along the drive shaft, such as an abrasive burr, a mass, a weight, a counterweight, a change in the size and/or shape of the drive shaft coils, or anything else that is distinguishable from the generally featureless drive shaft.

In general, the drive shaft may include at least one helically-wound coil that surrounds the guide wire, so that the guide wire may be translated longitudinally with respect to the drive shaft. In other words, the guide wire may be advanced and retracted longitudinally with respect to the drive shaft, and/or the drive shaft may be advanced and retracted longitudinally with respect to the guide wire. This advancing and/or retracting may be performed at any suitable time before, during and/or after the stenosis is removed.

When the atherectomy device includes only a single element, such as a single abrasive burr, or a single portion of the drive shaft that has enlarged coils, there may be instability during operation. For instance, when the single element is rotated rapidly around the rotational axis of the drive shaft, the single element may be deflected rather easily, leading to an irregular orbital motion of the element, and possible damage to the inside of the vessel being cleaned.

In order to increase stability, one may be tempted to merely increase the mass of the single element. This increased mass may provide an increased resistance to deflection, but if the element is eccentric (having its center of mass laterally displaced from the rotational axis of the drive shaft), then the increase in mass may reduce the stability of the orbital motion itself, simply by having too much mass too far off axis. This increase in eccentric mass may lead to damage of the drive shaft and/or the guide wire at high rotational velocities.

An improvement over simply increasing the mass of a single element is to provide one or more counterweights to the element, longitudinally separated from the element along the drive shaft. Taken as a whole, the increase in mass does increase stability during operation, but having the mass increased at locations proximally and/or distally, with respect to the single element, may increase the stability without deteriorating the orbital motion of the single element.

In some cases, the increase in mass may be a proximal counterweight and a distal counterweight, which are disposed longitudinally along the drive shaft on either side of an abrasive element. The following paragraphs describe various configurations for these counterweights.

In some cases, the abrasive element may be located halfway between the proximal and distal counterweights. In other applications, the abrasive element may be closer to one counterweight than to the other.

In some cases, the proximal and distal counterweights may have equal masses. In some cases, the proximal and distal counterweights may both have masses equal to half that of the abrasive element. In some cases, the proximal and distal counterweights may both have masses equal to half that of the abrasive element, and the abrasive element may be longitudinally located halfway between the counterweights.

In some cases, the abrasive element may be eccentric. In some cases, the abrasive element may be eccentric, with both counterweights being eccentric. In other applications, the abrasive element may be eccentric, with one counterweight being eccentric and the other counterweight being concentric. In some of these applications, the counterweights and abrasive element may have a combined center of mass that is coincident with the rotational axis of the drive shaft. In other of these applications, the counterweights and abrasive element may have a combined center of mass that is laterally displaced from the rotational axis of the drive shaft.

In some cases, the abrasive element may be concentric. In some cases, the abrasive element may be concentric, with both counterweights being concentric. In other applications, the abrasive element may be concentric, with both counterweights being concentric but on opposite sides of the drive shaft so that their combined center of mass is generally coincident with the rotational axis of the drive shaft. In still other applications, the abrasive element may be concentric, with both counterweights being concentric but on the same side of the drive shaft so that their combined center of mass is generally laterally displaced away from the rotational axis of the drive shaft.

In some cases, there may be more than one proximal counterweight, and/or more than one distal counterweight. In some cases, adjacent counterweights may be eccentric, with lateral displacements being on opposite sides of the drive shaft from each other so that their combined center of mass is roughly coincident with the rotational axis of the drive shaft.

In some cases, at least one counterweight may be generally round in shape, with a generally smooth exterior surface. This may help reduce any unwanted damage to the inside of the vessel during use.

In some cases, the guide wire may remain extended throughout the interior of the drive shaft during use, and may even extend out to the distal end of the drive shaft or beyond. This may increase the stability of the overall atherectomy device, because the local stiffness of the guide wire may be greater than that of the drive shaft, but may reduce the amplitude of the orbital motion of any eccentric elements on the drive shaft. However, the guide wire may experience unwanted flexional stress under these conditions.

In other applications, the guide wire may be partially or fully retracted from the distal end of the drive shaft prior to (or during) use. Without the locally stiff guide wire inside, the drive shaft is free to flex more as it is rotated under the influence of centrifugal force, compared with when the guide wire remains inside. As a result, for a given rotational speed and element size, an eccentric element without a guide wire therethrough may extend farther away from the rotational axis during high speed rotation and may therefore produce a desirably larger cutting diameter. Depending on the stiffnesses, flexions and/or flexibility of the materials involved, this increase in cutting diameter may be up to a factor of four or more.

This retraction of the guide wire may be advantageous in several ways. For instance, if one of the design goals is to achieve a particular cutting diameter for a given rotation speed, then the rest diameter of the eccentric abrasive element may be reduced if the guide wire is retracted, compared to when the guide wire is left extended throughout the drive shaft during use. In other words, a smaller abrasive element may achieve the desired cutting diameter if the guide wire is retracted prior to (or during) use, all other things being equal. Having a smaller abrasive element may be advantageous in that it may be easier to feed such a smaller element through the vasculature of the patient, in that it is less easily blocked, is more easily maneuvered, and may cause less incidental damage to the inside of the vessel before and after use.

In addition, the guide wire, being retracted, will experience less flexional stress and therefore may be less susceptible to breakage, thereby further reducing the risk of damage to the inside of the vessel being cleaned.

In some cases, the guide wire extends to the distal end, or beyond the distal end, of the drive shaft during use. In some cases, the guide wire may be retracted to the distal counterweight prior to, or during, use. In some cases, the guide wire may be retracted to the abrasive element prior to, or during, use. In some cases, the guide wire may be retracted to the proximal counterweight prior to, or during, use. In some cases, the guide wire may be retracted beyond the proximal counterweight prior to, or during, use.

FIGS. 10-17 are cross-section schematic drawings of a portion of a drive shaft 120 that includes an abrasive element 121C, 121E with an abrasive portion 122 on it, a proximal counterweight 123C, 123E and a distal counterweight 124C, 124E. The rotational axis 125 extends through the center of the drive shaft 120. For simplicity, the individual coils of the drive shaft 120 are not shown. The elements 121C, 121E, 123C, 123E, 124C and 124E are shown merely as circular in these figures, but it will be understood that any or all of the elements may be an abrasive burr, a mass, a weight, a counterweight, a change in the size and/or shape of the drive shaft coils, or anything else that is distinguishable from the generally featureless drive shaft 120.

Figure 10:
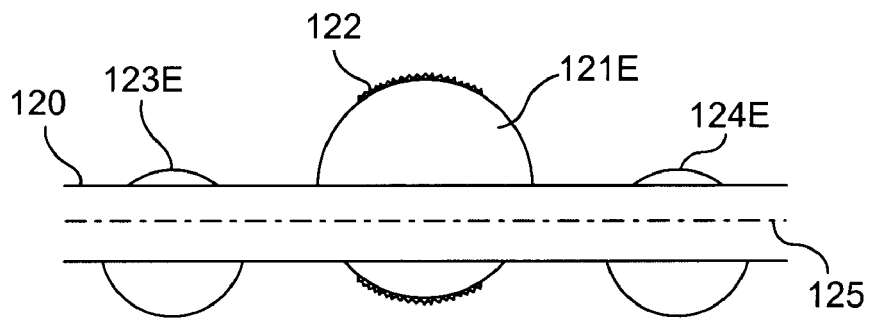
FIG. 10 is a cross-sectional drawing of an eccentric abrasive element, an eccentric proximal counterweight and an eccentric distal counterweight.
Figure 11:
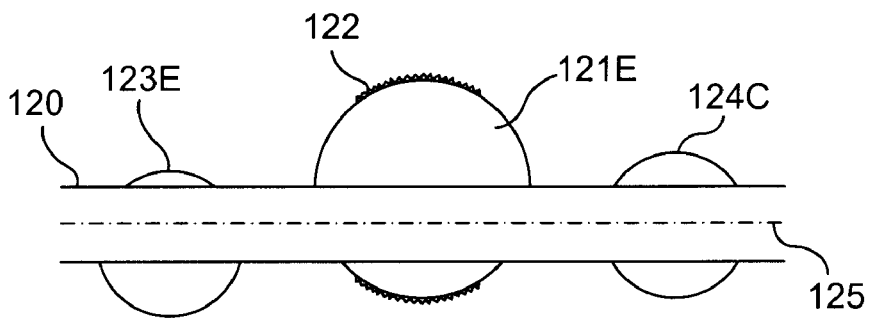
FIG. 11 is a cross-sectional drawing of an eccentric abrasive element, an eccentric proximal counterweight and a concentric distal counterweight.
Figure 12:
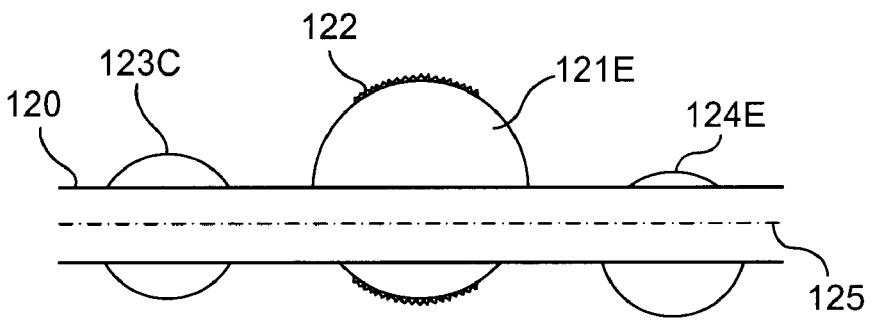
FIG. 12 is a cross-sectional drawing of an eccentric abrasive element, a concentric proximal counterweight and an eccentric distal counterweight.
Figure 13:
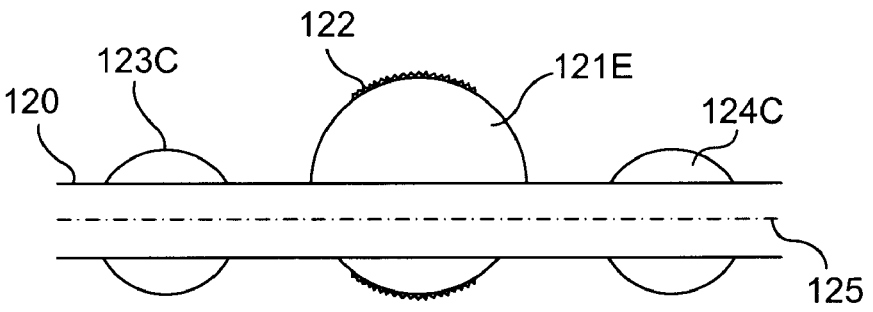
FIG. 13 is a cross-sectional drawing of an eccentric abrasive element, a concentric proximal counterweight and a concentric distal counterweight.
Figure 14:
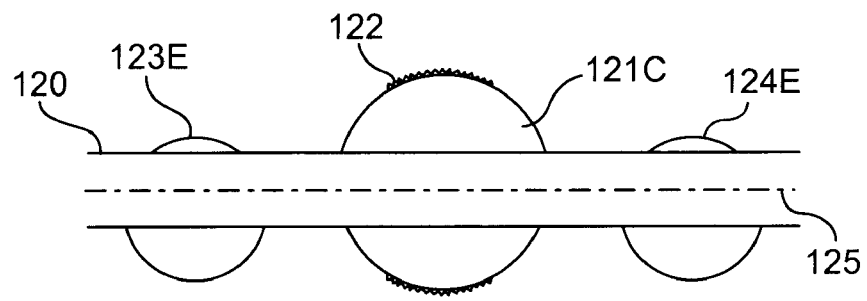
FIG. 14 is a cross-sectional drawing of a concentric abrasive element, an eccentric proximal counterweight and an eccentric distal counterweight.
Figure 15:
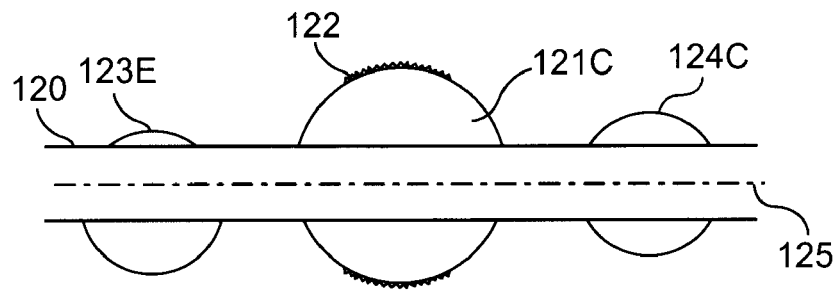
FIG. 15 is a cross-sectional drawing of a concentric abrasive element, an eccentric proximal counterweight and a concentric distal counterweight.
Figure 16:
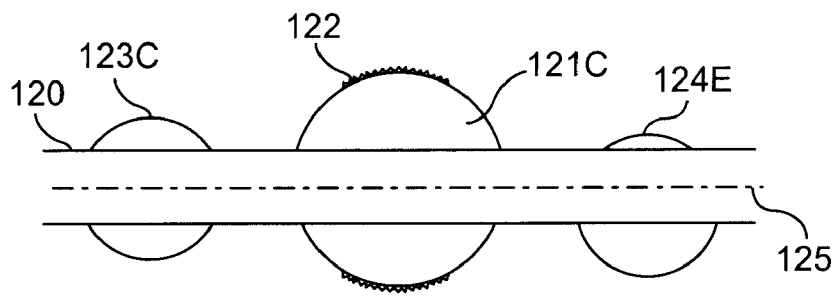
FIG. 16 is a cross-sectional drawing of a concentric abrasive element, a concentric proximal counterweight and an eccentric distal counterweight.
Figure 17:
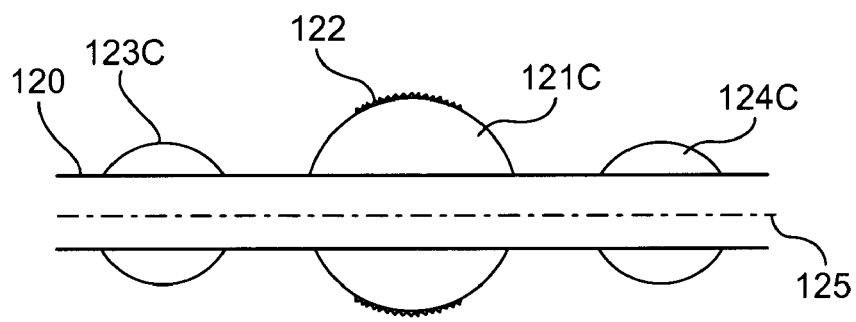
FIG. 17 is a cross-sectional drawing of a concentric abrasive element, a concentric proximal counterweight and a concentric distal counterweight.

FIG. 10 shows an eccentric abrasive element 121E, an eccentric proximal counterweight 123E and an eccentric distal counterweight 124E. FIG. 11 shows an eccentric abrasive element 121E, an eccentric proximal counterweight 123E and a concentric distal counterweight 124C. FIG. 12 shows an eccentric abrasive element 121E, a concentric proximal counterweight 123C and an eccentric distal counterweight 124E. FIG. 13 shows an eccentric abrasive element 121E, a concentric proximal counterweight 123C and a concentric distal counterweight 124C. FIG. 14 shows a concentric abrasive element 121C, an eccentric proximal counterweight 123E and an eccentric distal counterweight 124E. FIG. 15 shows a concentric abrasive element 121C, an eccentric proximal counterweight 123E and a concentric distal counterweight 124C. FIG. 16 shows a concentric abrasive element 121 C, a concentric proximal counterweight 123C and an eccentric distal counterweight 124E. FIG. 17 shows a concentric abrasive element 121C, a concentric proximal counterweight 123C and a concentric distal counterweight 124C.

Figure 18:
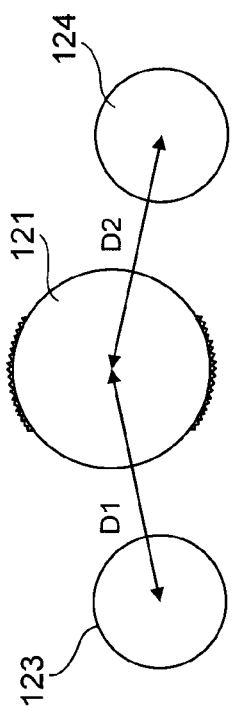
FIG. 18 is a schematic drawing of the abrasive element and counterweights, with a distance D1 between the centers of mass of proximal counterweight and abrasive element, and a distance D2 between the centers of mass of distal counterweight and abrasive element.

FIG. 18 is a schematic drawing of the abrasive element 121 and counterweights 123 and 124, with a distance D1 between the centers of mass of proximal counterweight 123 and abrasive element 121, and a distance D2 between the centers of mass of distal counterweight 124 and abrasive element 121. In some cases, D1 equals D2. In other cases, D1 is different from D2. Note that D1 and D2 are shown in FIG. 18 as being the distances between the centers of mass of the various elements; alternatively, D1 and D2 may denote the longitudinal distances along the rotational axis of the drive shaft.

In some cases, the distances D1 and D2 may be controllable and/or adjustable. For instance, for counterweights that are manufactured separately from the drive shaft and then attached to the drive shaft (as opposed to being made integral with the drive shaft), it may be possible to unlock a counterweight, slide it to a new location along the drive shaft, thereby producing a new value for D1 and/or D2, and lock the counterweight to the drive shaft at the new location. The sliding may be initiated mechanically, such as by a sliding wire that can slide parallel to, but independent of, the guide wire. Such a sliding wire may be adjacent to and parallel to the guide wire, or may be concentric with the guide wire, being inside the guide wire or outside the guide wire. Alternatively, the sliding may be initiated magnetically, such as by a magnet or magnetic element that attracts or repels the counterweight. The locking mechanism may use a clamp, a grip/snare, or other known ways of locking an element to another element, so that the element or elements may be removably clamped to the drive shaft. Preferably, the unlocking, sliding and locking takes place when the atherectomy device is not being used to remove the stenosis; such actions should take place at relatively low rotational speeds or when the device is rotationally stationary.

FIGS. 19-23 show the guide wire 136 being extended through the drive shaft 130 at various locations during and/or prior to use.

Note that in this series of figures, the abrasive element and counterweights are all eccentric and are all formed by enlarged portions of the drive shaft. The enlarged portions of the drive shaft may include enlargements on only one side of the drive shaft, or both sides of the drive shaft, as in FIGS. 19-23. Any or all of the enlargements may be asymmetric, in that the center of mass of the enlargement may be laterally offset from the rotational axis of the drive shaft; this is the case in the exemplary eccentric elements of FIGS. 19-23. Alternatively, any or all of the enlargements may be symmetric with respect to the rotational axis of the drive shaft, making the respective element concentric.

It will be understood that for all examples throughout this application, an enlarged portion of the drive shaft may be interchangeable with an element attached to the drive shaft. For FIGS. 19-23, we simply choose to draw enlarged portions of the drive shaft, although attached elements may also be used.

Figure 19:
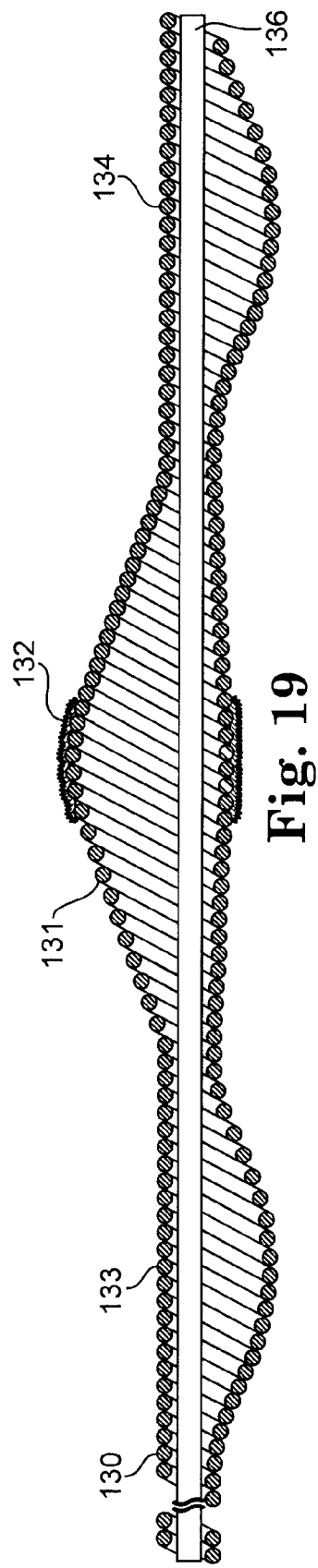
FIG. 19 is a cross-sectional drawing of the guide wire extending beyond the distal end of the drive shaft during operation.
Figure 20:
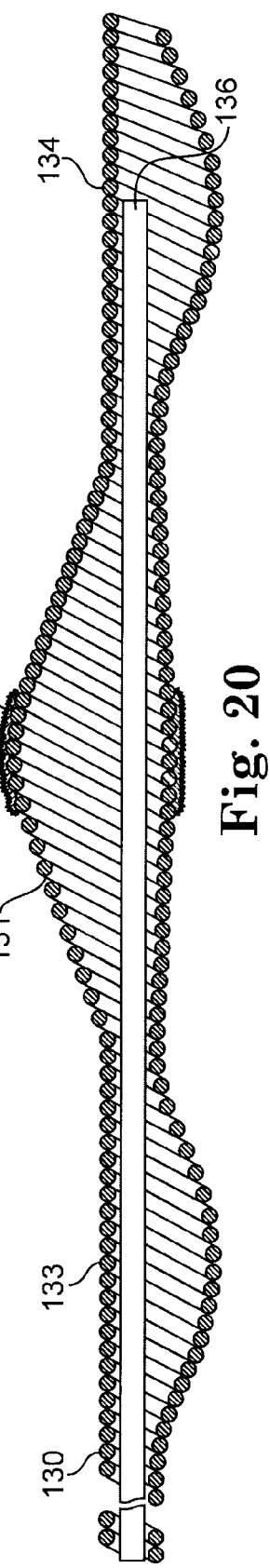
FIG. 20 is a cross-sectional drawing of the guide wire retracted to the distal counterweight prior to and/or during operation.
Figure 21:
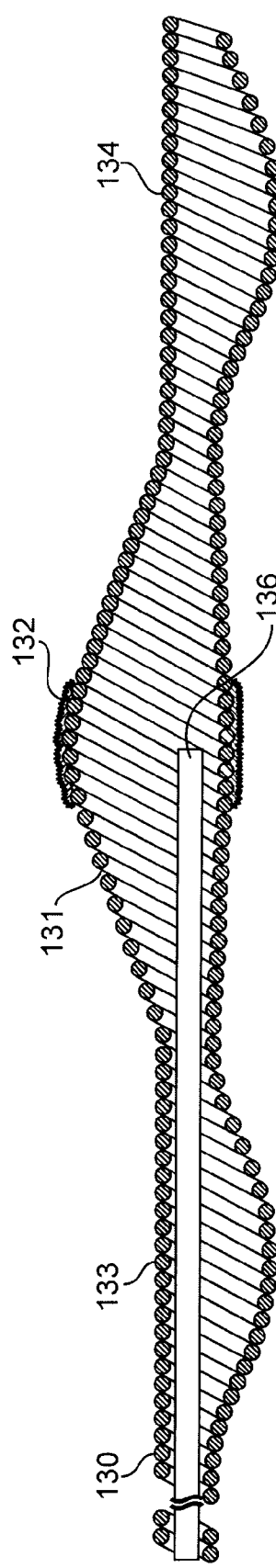
FIG. 21 is a cross-sectional drawing of the guide wire retracted to the abrasive element prior to and/or during operation.
Figure 22:
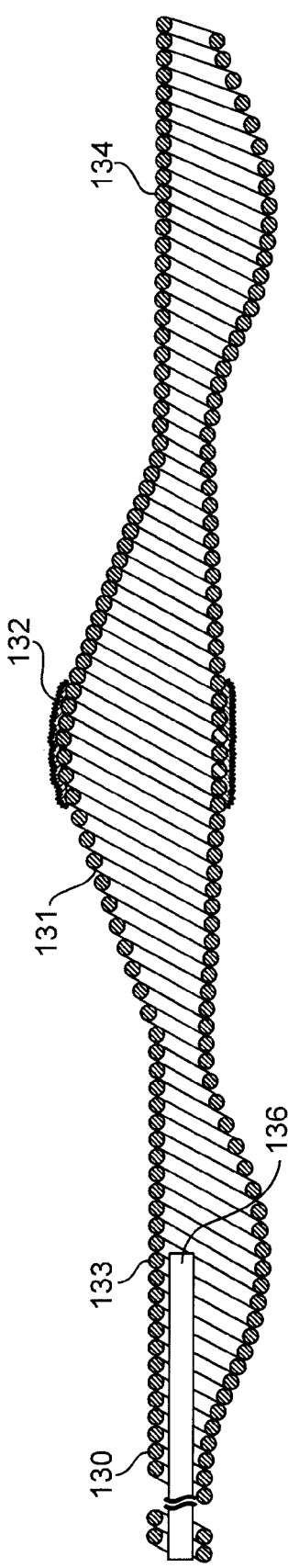
FIG. 22 is a cross-sectional drawing of the guide wire retracted to the proximal counterweight prior to and/or during operation.
Figure 23:
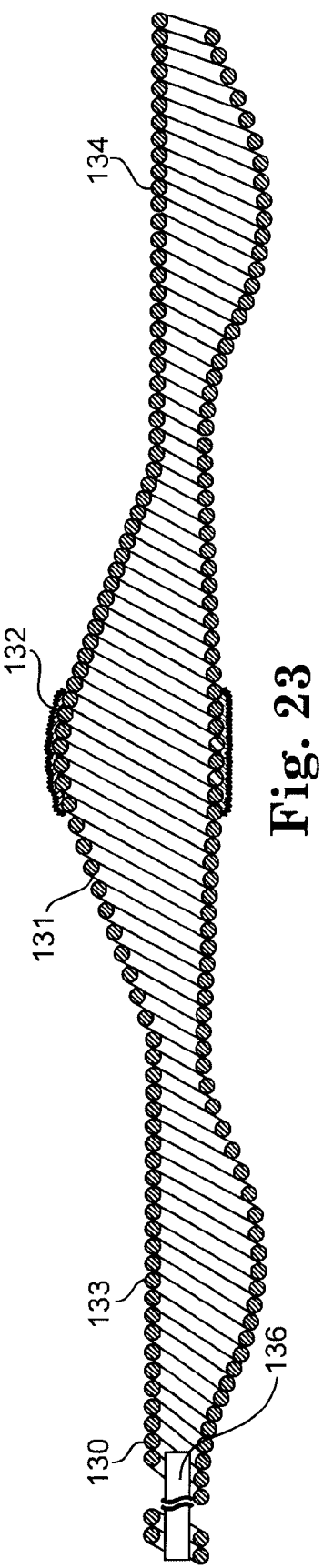
FIG. 23 is a cross-sectional drawing of the guide wire retracted beyond the proximal counterweight prior to and/or during operation.

FIG. 19 has the guide wire 136 extended beyond the distal end of the drive shaft 130 during operation. FIG. 20 has the guide wire 136 retracted to the distal counterweight 134 prior to and/or during operation. FIG. 21 has the guide wire 136 retracted to the abrasive element 131 prior to and/or during operation. FIG. 22 has the guide wire 136 retracted to the proximal counterweight 133 prior to and/or during operation. FIG. 23 has the guide wire 136 retracted beyond the proximal counterweight 133 prior to and/or during operation.

In FIGS. 19-23, the abrasive portion 132 includes a band of abrasive that extends fully around the drive shaft. Alternatively, the abrasive portion may extend only across a portion of the drive shaft, with no abrasive on the relatively flat side.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. A high-speed rotational atherectomy device for opening a stenosis in an artery having a given diameter, comprising: a guide wire having a maximum diameter less than the diameter of the artery; a flexible, elongated, rotatable drive shaft advanceable over the guide wire; an eccentric abrasive element disposed on the drive shaft; a proximal counterweight attached to the drive shaft and spaced apart proximally from the eccentric abrasive element by an adjustable proximal spacing; and a distal counterweight attached to the drive shaft and spaced apart distally from the eccentric abrasive element by an adjustable distal spacing, wherein the proximal and distal counterweights are held in place by a locking mechanism and wherein adjustable proximal and distal spacings from the eccentric abrasive element are achieved by unlocking the locking mechanism and sliding the proximal and distal counterweights along the drive shaft and then locking the locking mechanism when the proximal and distal spacings are achieved.

2. The high-speed rotational atherectomy device of claim 1, wherein the locking mechanism comprises a clamp and wherein the proximal counterweight is removably clampable to the drive shaft, wherein the proximal counterweight is clamped to the drive shaft at the adjustable proximal spacing from the eccentric abrasive element for high-speed rotation of the drive shaft, and wherein the proximal counterweight is unclamped for adjustment of the proximal spacing, the adjustment occurring at low-speed rotation or non-rotation of the drive shaft.

3. The high-speed rotational atherectomy device of claim 2, wherein the proximal counterweight is slidable along the drive shaft when the proximal counterweight is unclamped.

4. The high-speed rotational atherectomy device of claim 1, wherein the locking mechanism comprises a clamp and wherein the distal counterweight is removably clampable to the drive shaft, wherein the distal counterweight is clamped to the drive shaft for high-speed rotation of the drive shaft, and wherein the distal counterweight is unclamped for adjustment of the distal spacing, the adjustment occurring at low-speed rotation or non-rotation of the drive shaft.

5. The high-speed rotational atherectomy device of claim 4, wherein the distal counterweight is slidable along the drive shaft when the distal counterweight is unclamped.

6. The high-speed rotational atherectomy device of claim 1, wherein the eccentric abrasive element comprises an eccentric abrasive crown attached to the drift shaft.

7. The high-speed rotational atherectomy device of claim 1, wherein the eccentric abrasive element comprises an eccentric enlarged abrasive section of the drive shaft.

* * * * *